United States Patent
Milo (10) Patent No.: US 9,610,097 B2
(45) Date of Patent: Apr. 4, 2017

(54) DEVICE FOR CREATING TEMPORARY ACCESS AND THEN CLOSURE

(71) Applicant: Simcha Milo, Haifa (IL)

(72) Inventor: Simcha Milo, Haifa (IL)

(*) Notice: Subject to any disclaimer, the term of this patent is extended or adjusted under 35 U.S.C. 154(b) by 156 days.

(21) Appl. No.: 14/168,890

(22) Filed: Jan. 30, 2014

(65) Prior Publication Data

US 2014/0148786 A1 May 29, 2014

Related U.S. Application Data

(63) Continuation of application No. PCT/IB2012/001606, filed on Aug. 20, 2012.

(Continued)

(51) Int. Cl.
*A61B 17/32* (2006.01)
*A61B 17/34* (2006.01)
(Continued)

(52) U.S. Cl.
CPC ...... *A61B 17/3468* (2013.01); *A61B 17/3423* (2013.01); *A61B 17/068* (2013.01);
(Continued)

(58) Field of Classification Search
CPC . A61B 17/34; A61B 17/3417; A61B 17/3423; A61B 17/10; A61B 17/08;
(Continued)

(56) References Cited

U.S. PATENT DOCUMENTS

| 4,204,541 A | 5/1980 | Kapitanov |
| 4,991,578 A * | 2/1991 | Cohen .................. A61N 1/0587 607/2 |

(Continued)

FOREIGN PATENT DOCUMENTS

| WO | 2006/020651 | 2/2006 |
| WO | 2007/098212 | 8/2007 |

(Continued)

OTHER PUBLICATIONS

International Search Report, dated Jan. 25, 2013 for International Application No. PCT/IB2012/001606 (7 pgs.).

(Continued)

*Primary Examiner* — David C Eastwood
(74) *Attorney, Agent, or Firm* — Fitch, Even, Tabin & Flannery LLP (57) ABSTRACT

Devices (11, 111) for providing temporary access to the ventricle of the heart and then closing such an access passage when the operation demanding such access has been completed. These devices include an anchor (13, 113) with a wire spiral (19, 119) for implantation in the tissue wall of the heart and a handle (15, 115) detachably connected to the anchor. The handle provides an axial passageway in which a hollow needle (27, 127) is slidably and stably received. With the anchor in juxtaposition with the apex of the heart, the pointed end of the hollow needle is inserted into the ventricle, and its presence traversing the wall of the heart provides a stable axis about which the wire spiral (19, 119) can be rotated to seat the anchor in precise circumscribing fashion about the hollow needle (27, 127).

15 Claims, 9 Drawing Sheets

Related U.S. Application Data (60) Provisional application No. 61/526,374, filed on Aug. 23, 2011.

(51) Int. Cl.
*A61B 17/068* (2006.01)
*A61B 17/00* (2006.01)
*A61B 17/064* (2006.01)

(52) U.S. Cl.
CPC .......... *A61B 2017/00247* (2013.01); *A61B 2017/00353* (2013.01); *A61B 2017/00575* (2013.01); *A61B 2017/00623* (2013.01); *A61B 2017/0649* (2013.01); *A61B 2017/3425* (2013.01); *A61B 2017/3484* (2013.01); *A61B 2017/3488* (2013.01)

(58) Field of Classification Search
CPC . A61B 17/083; A61B 17/3468; A61B 17/068; A61B 2071/00575; A61B 2071/081; A61B 2071/349; A61B 2071/00247; A61B 2071/3425; A61B 2071/3427; A61B 2071/3454; A61B 2071/3458; A61B 2071/348; A61B 2071/3482; A61B 2071/3484; A61B 2071/00353; A61B 2071/0649; A61B 2071/3488; A61B 2071/00623
USPC .................................................. 606/185, 213
See application file for complete search history.

(56) References Cited

U.S. PATENT DOCUMENTS

| | | | |
|---|---|---|---|
| 5,356,424 A | 10/1994 | Buzerak et al. | |
| 5,407,427 A * | 4/1995 | Zhu ................... | A61B 17/0281 604/26 |
| 5,782,844 A | 7/1998 | Yoon et al. | |
| 5,810,851 A * | 9/1998 | Yoon .................. | A61B 17/06 606/139 |
| 6,468,309 B1 * | 10/2002 | Lieberman .......... | A61F 2/446 606/77 |
| 6,488,683 B2 * | 12/2002 | Lieberman .......... | A61B 17/70 606/263 |
| 6,527,774 B2 * | 3/2003 | Lieberman .......... | A61B 17/70 606/301 |
| 6,986,784 B1 * | 1/2006 | Weiser ................ | A61F 2/2493 606/108 |
| 7,033,372 B1 * | 4/2006 | Cahalan ............. | A61B 17/3478 128/898 |
| 7,534,260 B2 | 5/2009 | Lattouf | |
| 7,846,123 B2 | 12/2010 | Vassiliades et al. | |
| 8,099,177 B2 * | 1/2012 | Dahlberg ............ | A61N 1/05 607/127 |
| 8,920,456 B2 * | 12/2014 | Kadykowski ........ | A61B 1/015 600/156 |
| 2002/0026176 A1 * | 2/2002 | Varner ................ | A61F 9/0017 604/891.1 |
| 2002/0055738 A1 * | 5/2002 | Lieberman .......... | A61B 17/70 623/17.11 |
| 2002/0183786 A1 * | 12/2002 | Girton ................ | A61B 17/0057 606/213 |
| 2003/0073972 A1 * | 4/2003 | Rosenman .......... | A61B 17/3468 604/502 |
| 2004/0143314 A1 * | 7/2004 | Sommer ............. | A61M 25/0082 607/120 |
| 2005/0251240 A1 * | 11/2005 | Doan .................. | A61N 1/0573 607/127 |
| 2006/0009800 A1 | 1/2006 | Christianson et al. | |
| 2006/0089707 A1 | 4/2006 | Vassiliades et al. | |
| 2008/0004640 A1 * | 1/2008 | Ellingwood ........ | A61B 17/0057 606/151 |
| 2008/0269662 A1 * | 10/2008 | Vassiliades ......... | A61B 17/32053 604/8 |
| 2009/0157174 A1 | 6/2009 | Yoganathan et al. | |
| 2009/0177219 A1 * | 7/2009 | Conlon ............... | A61B 17/3478 606/185 |
| 2009/0240264 A1 * | 9/2009 | Tuval ................. | A61B 17/0469 606/148 |
| 2009/0259212 A1 * | 10/2009 | Sabbah .............. | A61M 25/0084 604/511 |
| 2010/0030328 A1 * | 2/2010 | Seguin ............... | A61B 17/064 623/2.11 |
| 2010/0168778 A1 | 7/2010 | Braido | |
| 2010/0261974 A1 * | 10/2010 | Shelton, IV ........ | A61B 17/3423 600/208 |
| 2010/0274091 A1 | 10/2010 | Rothstein et al. | |
| 2010/0292785 A1 * | 11/2010 | Seguin ............... | A61B 17/00234 623/2.11 |
| 2011/0028985 A1 | 2/2011 | Vassiliades et al. | |
| 2011/0028995 A1 * | 2/2011 | Miraki ............... | A61B 17/0482 606/144 |
| 2011/0190811 A1 | 8/2011 | Shanley | |
| 2012/0089181 A1 * | 4/2012 | Shanley ............. | A61B 17/0057 606/223 |
| 2012/0123461 A1 * | 5/2012 | Gillies ............... | A61B 17/3423 606/185 |
| 2013/0338706 A1 * | 12/2013 | Jimenez ............ | A61B 17/0057 606/213 |
| 2015/0133970 A1 * | 5/2015 | Ranucci ............ | A61B 17/064 606/151 |

FOREIGN PATENT DOCUMENTS

| | | |
|---|---|---|
| WO | 2008/131453 | 10/2008 |
| WO | 2009/079091 | 6/2009 |
| WO | 2009/117435 | 9/2009 |
| WO | 2011/057299 | 5/2011 |
| WO | 2011/156782 | 12/2011 |

OTHER PUBLICATIONS

Written Opinion of the International Searching Authority for International Application No. PCT/IB2012/001606 (9 pgs.).
International Preliminary Report on Patentability, date of issuance Feb. 25, 2014 for International Application No. PCT/IB2012/001606 (10 pgs.).
Communication regarding comments on written opinion/amendment of application/payment of claims fee, dated Apr. 29, 2014 for European Applicaiton No. 12762386.6 (2 pgs.).
Response to Communication pursuant to Rule s161(1) and 162 EPC (Apr. 29, 2014 ), Dated Nov. 7, 2014 for European Applicaiton No. 12762386.6 (17 pgs.).
First Examination Report from the European Patent Office, dated Aug. 6, 2015 for European Applicaiton No. 12762386.6 (5 pgs.).
Response to Communication pursuant to Article 94(3) EPC (Aug. 6, 2015), dated Feb. 12, 2016 for European Applicaiton No. 12762386.6 (6 pgs.).
Communication about intention to grant European patent, dated Jul. 1, 2016 for European Applicaiton No. 12762386.6 (64 pgs.).

* cited by examiner

A patent document page.

DEVICE FOR CREATING TEMPORARY ACCESS AND THEN CLOSURE

This application is a continuation of International Application No. PCT/IB2012/001606, filed Aug. 20, 2012, and claims priority from U.S. Provisional Application No. 61/526,374, filed Aug. 23, 2011, the disclosures of both which are incorporated herein by reference.

This invention provides devices for providing temporary access into an organ of the body and more particularly to devices for providing temporary access to a ventricle of the heart and then readily closing such access, as well as to methods for using such devices. Still more particularly, the invention relates to devices useful in transapical aortic-valve implantations (TAVI) and other such generally related procedures.

BACKGROUND OF THE INVENTION

Providing access to a bodily organ, particularly a ventricle of a heart, is necessary for a number of procedures, including the repair of ventricular defects as well as the repair or replacement of a mitral or aortic valve. There are many methods that have been developed for carrying out such procedures, a great number of which involve cardio-pulmonary bypass. Sternotomy or side thoracotomies with connection to Cardio-pulminory bypass (CPB) are methods usually used during such operations. However, particular patients may fall within a high risk category that would dictate avoidance of such procedures. In the last decade or so, the ability to stabilize a beating heart has allowed access to the heart via the apex of the heart for such repair and/or valve replacement. Recently, transapical aortic valve implantation (TAVI) has become practicable, and in many instances, it may be preferable to percutaneous implantation via the femoral artery.

As a result, there has been an impetus to design devices for providing access to an organ, particularly a ventricle of a heart, in a manner so that, upon completion of the operable procedure, closure of such entry passage can be simply and readily effected.

SUMMARY OF THE INVENTION

The invention provides devices for providing an entry passageway into a bodily organ, such as the ventricle of a heart through its apex, using a hollow needle to permit a simple operation such as withdrawal of fluid or a more complex operation, such as TAVI or the like, and upon completion, for effectively and readily closing such entry passageway. The entry passageway, once established and then defined by the introduction of a guidewire for a TAVI or the like, allows the insertion and the exchange of one or more catheters, using the "over the wire" technique, with minimal harm to the tissue while such transapical procedures are carried out. Once such operation has been completed, the device is used to compress the tissue and effectively seal the entry passageway created initially by the hollow needle.

In one particular aspect, the invention provides a device for providing temporary access to a ventricle of the heart, which device comprises an anchor which includes a ring-shaped body having a central opening and at least one wire spiral having a pointed distal end and having a proximal end that is connected to said body, which wire spiral is shaped for juxtaposition with the exterior surface of the apex of the heart, a detachable handle having a base formed with a central aperture and an interconnection means which links said base to said anchor, said handle including an elongated guide section that is formed with an elongated central passageway open at opposite ends, an elongated, hollow needle having a pointed tip for insertion through the wall of the heart so as to enter a ventricle thereof, which needle is slidably received in said elongated central passageway, and means securing said hollow needle to said guide section which limits the distance said hollow needle can be axially moved within said guide section while locating said pointed tip so that it penetrates the heart tissue before said wire spiral makes contact with the heart outer surface, whereby, once said needle is caused to penetrate into the heart ventricle, the device can be readily attached to the heart wall at the apex by screwing the wire spiral into the tissue wall of the heart via rotation about said needle as an axis, so that the device will then provide access to the heart ventricle along a guide wire that extends through said anchor, which guide wire is inserted through the lumen of the hollow needle before the hollow needle is withdrawn.

In another particular aspect, the invention provides a device for providing a temporary access opening into a human heart and then effectively closing such access opening, which device comprises an anchor comprising a wire spiral formed of at least 2 spiral sections each having a pointed distal end, with proximal ends of said spiral sections inter-connected to one another, which wire spiral is shaped for juxtaposition with the exterior surface of the heart, a detachable handle having a central passageway that is aligned axially of the wire spiral, said handle and said anchor being formed for detachable interconnection with each other, and an elongated, hollow needle having a pointed tip for insertion through the wall of the apex of the heart so as to enter a cavity therewithin, said handle central passageway positioned to guide movement of said hollow needle axially within said wire spiral, whereby said needle is slidable within said handle and once having entered the heart ventricle provides an axis about which said wire spiral can be readily screwed into the tissue wall of the heart symmetrically about said needle, wherein said wire spiral is so shaped that, after said needle is removed from the ventricle, said device can close the passage through the heart apex by further rotating the wire spiral so that the tissue is uniformally compressed radially inward toward the passage created by the hollow needle.

In a further particular aspect, the invention provides a method for providing temporary access to a ventricle of the heart by passage through the apex and then sealing such passage, which method comprises the steps of inserting an elongated, hollow needle having a pointed tip through the wall of the apex of the heart so as to enter a ventricle thereof, which needle is positioned within a rotatable anchor that includes at least one wire spiral having a pointed distal end and having a proximal end that will remain exterior of the surface of the apex of the heart, with said needle penetrating into the heart ventricle, screwing the rotatable wire spiral into the tissue wall of the heart via rotation about said needle as an axis using a detachable handle connected to the anchor, which handle has a central passageway within which said hollow needle can be axially moved, subsequently withdrawing said hollow needle from the ventricle and separating it from the anchor, after the hollow needle is withdrawn, closing the passage initially created by the hollow needle by screwing the wire coil deeply into the wall of the heart at its apex to radially compress heart wall tissue inward to seal such passage, and then detaching and removing the handle.

DESCRIPTION OF THE DRAWINGS

FIG. 1 is a front view of a device for providing temporary access to a bodily organ such as the apex of a heart, which device embodies various features of the invention and is designed for use in connection with a TAVI operation or the like.

DETAILED DESCRIPTION OF THE PREFERRED EMBODIMENTS

Two devices which constitute preferred versions of devices for the purpose of providing temporary access to an organ in the body of a living person are illustrated and described hereinafter; however, it should be understood that although the description is given, for purposes of convenience, with respect to entry into the left ventricle of the human heart via the apex, the devices could be used in connection with access to other bodily organs in situations where temporary access is desired and it is important to be able to promptly and effectively close the passage created into that organ upon completion of the medical procedure requiring such access.

Disclosed in FIGS. 1-15, is one embodiment of a device for providing temporary access to a bodily organ, such as the ventricle of the heart, and then readily and effectively closing such an access passageway when the operation in question has been completed. The device 11 includes an anchor 13 and a composite handle 15, which are interconnected so that the anchor can be screwed into the tissue of a bodily organ, in this case the apex of the human heart.

Figure 1:
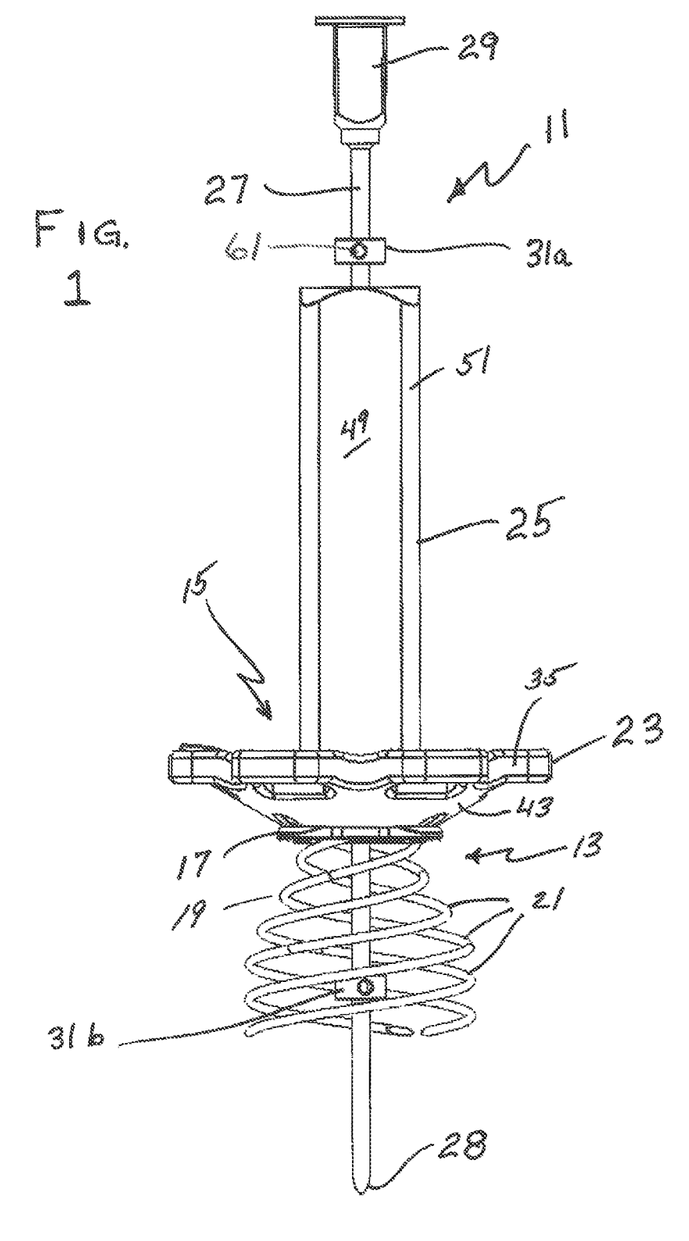
Figure 2:
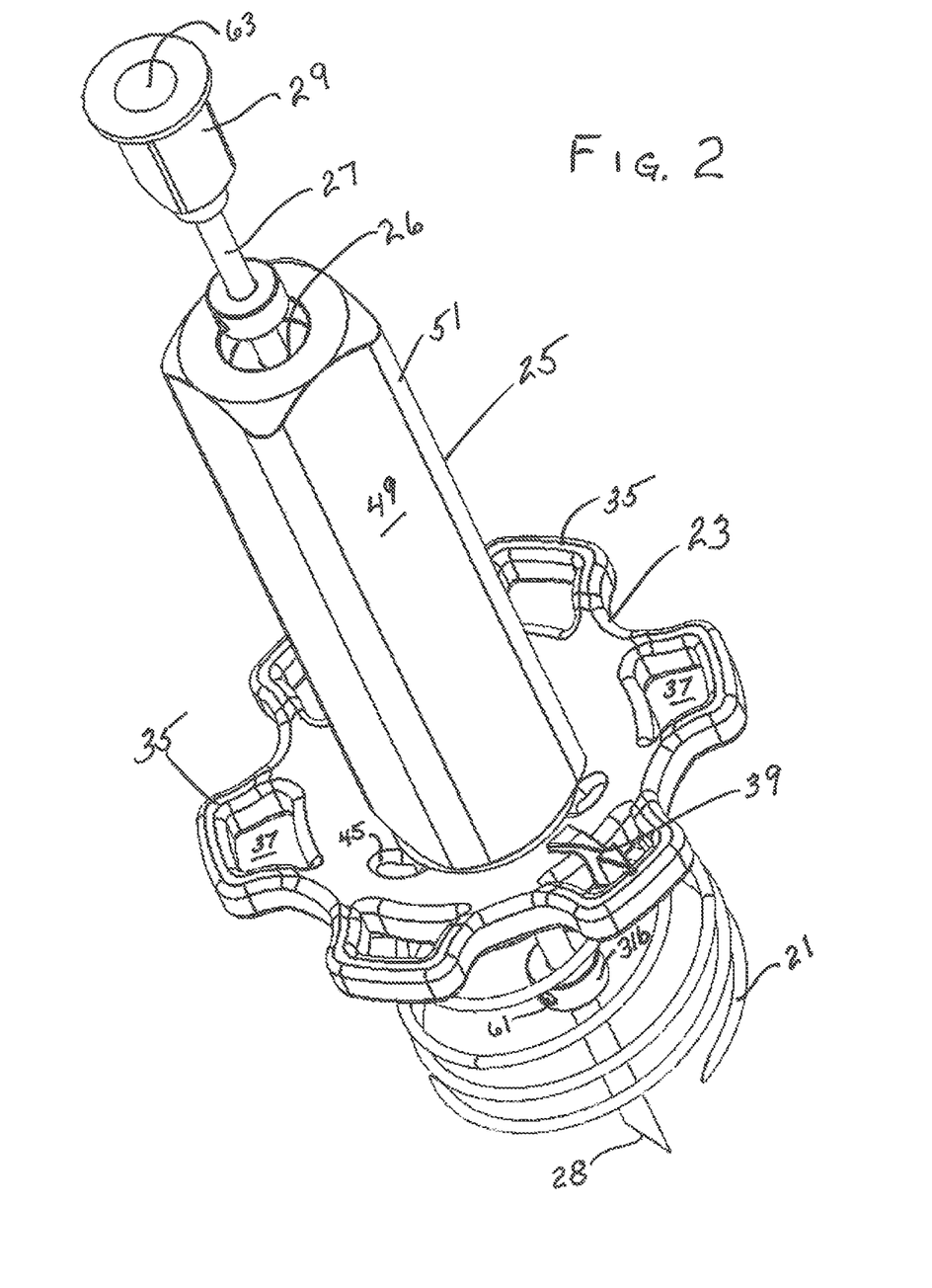
FIG. 2 is a perspective drawing of the device of FIG. 1 enlarged in size and viewed from above.
Figures 3, 3A:
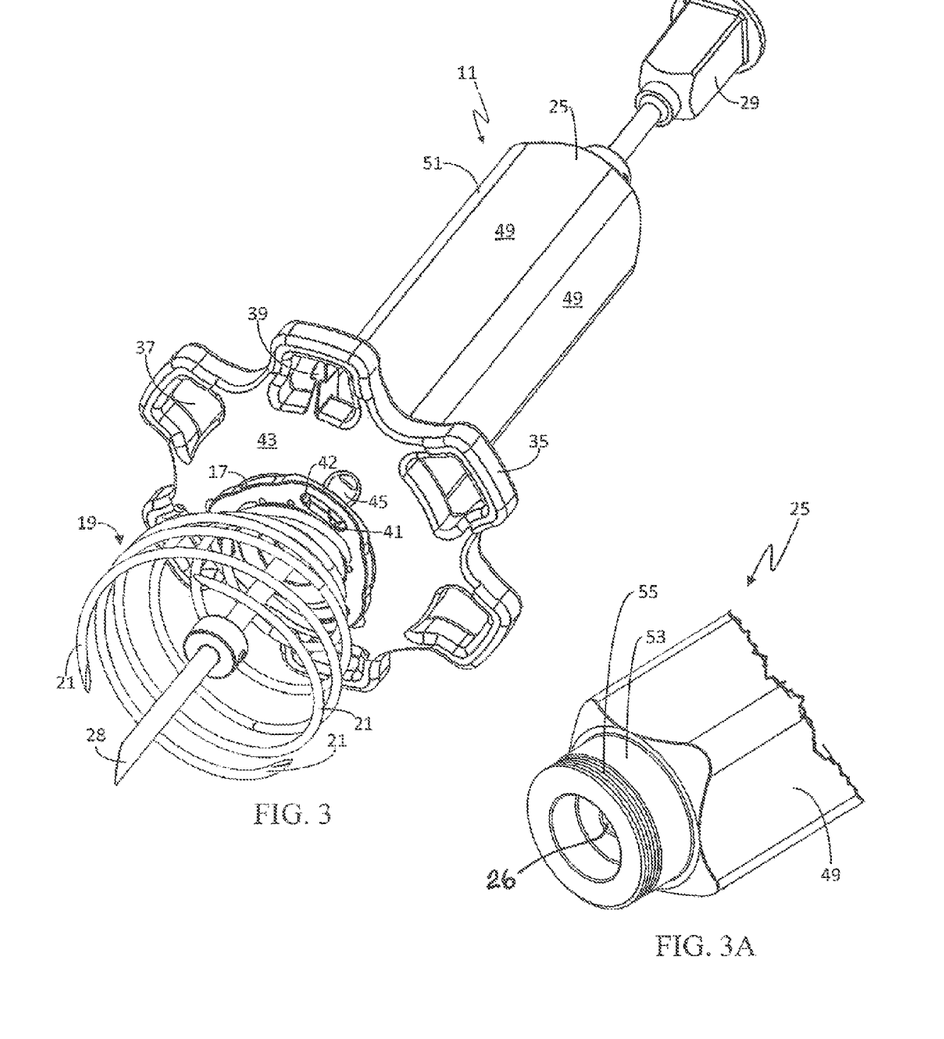
FIG. 3 is a perspective drawing of the device of FIG. 1 enlarged in size and drawn looking from below.
FIG. 3A is a fragmentary drawing of one component of the FIG. 3 device

The anchor includes a ring-shaped body 17 to which is affixed the proximal end of a wire spiral 19. The wire spiral 19 may comprise a plurality of wire spiral sections 21, for example 2, 3, 4 or more. Illustrated in FIGS. 1-3, is a wire spiral 19 comprising three spiral wire sections 21. The three wire sections 21 are connected to one another at the proximal ends thereof; in this case, they are interconnected by their respective attachments to the ring-shaped body 17 of the anchor. If the wire spiral sections 21 and the ring-shaped body 17 are made of medical grade biocompatible metal, such as Nitinol, it may be suitable for the proximal ends of the spiral wire sections to be welded to the ring. Alternative forms of suitable interconnection would be employed if different materials, for example biocompatible and/or bioabsorbable polymers, are used for construction of the ring and/or wire sections. Because once it has been securely closed, the passage heals and no longer requires compression, and as a result, bioabsorbables would be acceptable.

The composite handle 15 includes an annular handle base section 23 and an extended elongated guide section 25. The guide section is formed with a central passageway 26 within which an elongated hollow needle 27 is slidably received.

The hollow needle 27 has a pointed distal end 28 and a grip or actuator 29 at its proximal end, through which there is an extension of the interior lumen of the hollow needle 27. Proximal and distal stops or collars 31a and 31b determine the extent to which the hollow needle 27 can be moved relative to the elongated guide section 25 of the handle and also secure the hollow needle to the elongated guide section of the handle as a subassembly of device 11.

Figure 10:
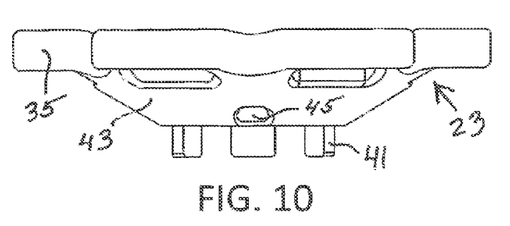
FIG. 10 is a front view of the handle base as seen in FIGS. 1-3.
Figure 10A:
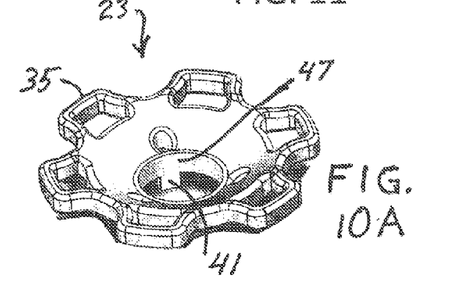
FIG. 10A is a perspective view, reduced in size, of the handle base of FIG. 10.

More specifically, the handle base 23 is annular, having a perimeter in the form of six tabs 35 that are arranged at 60 degree intervals and have windows 37 formed in them which allow the surgeon to view the organ below the handle. One of the windows 37 is formed with an arrow or other marker 39 to provide a point of reference so that the surgeon can determine more specifically how far he or she may have rotated the device using the handle in setting the wire coil 19 of the anchor in the tissue of the organ, e.g. the wall of the heart adjacent its apex. As best seen in FIG. 10A, the annular handle base 23 has a central aperture 47 of sufficient size, e.g. about 18-20 mm, to allow the distal collar 31b to pass therethrough upon removal of the hollow needle 27 and to allow passage for a catheter for a TAVI operation. The undersurface 43 or distal surface of the handle base 23, is formed with three equiangularly located prongs 41 (FIG. 10) which extend distally from the undersurface and which are received in three slots 42 in the ring-shaped body 17 of the anchor. This arrangement, as referred to hereinafter, allows the handle base 23 and the anchor 13 to be press-fit to each other.

Figure 12:
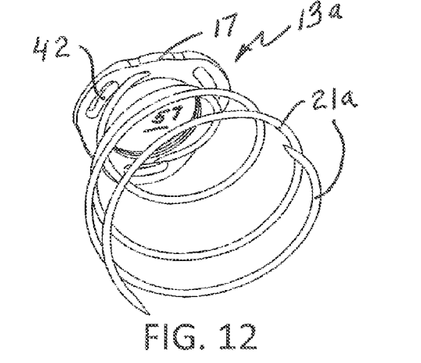
FIGS. 12 and 13 are perspective views of two alternative embodiments of representative anchors that might be employed as a part of the device shown in FIG. 1.
Figure 13:
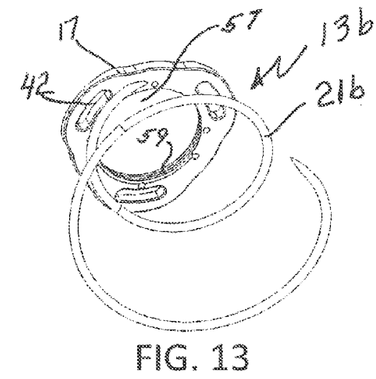

The extended guide section 25 of the handle is generally square in cross-section and is formed with four concave sidewalls 49 and four rounded edges 51, which allow a surgeon to grasp this section of the handle and rotate the handle and the interconnected anchor 13. The distal end of the extended guide is formed with a circular neck 53, as best seen in FIG. 3A, which is threaded to provide a threaded distal end 55. The ring-shaped body 17 of the anchor is formed with a central opening 57 that carries threads 59 which mate with the threads 55 on the extended guide section of the handle, as best seen in FIGS. 12 and 13.

Accordingly, the handle base 23 is press-fit to the ring-shaped body 17 of the anchor 13 through its three prongs 41 so turning the handle will cause the wire spiral sections 21 to enter the heart tissue. The extended guide section 25 of the handle has a neck 53 that is received in the central aperture 47 of the handle base, and its threaded end 55 is also connected to the ring-shaped body 17 by interengaging its threads 59.

The hollow needle 27 is circular in cross-section and may be about 3-4 mm in outer diameter. It is slidably received in the central passageway 26 formed in the extended guide section 25 of the handle, which serves to precisely guide the movement of the needle axially of the wire coil anchor with which it is aligned. To assure stable guidance, the length of the central passageway 26 should be at least 6 times the diameter of the needle, preferably at least about 10 times, and more preferably at least 15 times. For example, the extended guide section 25 may be about 8 cm long for such a needle 27. The distance of movement of the hollow needle 27 within the handle is limited by the positioning of the proximal collar 31a and the distal collar 31b. The collars 31 are affixed at the desired longitudinal locations along the hollow needle, as by small set screws 61. The central passageway 26 is open at each end, and the movement of the slidable needle therewithin is guided with the grip 29 at the proximal end of the needle. With the set screws 61 tightened, the collars 31 unite the needle 27 and the extended guide section 25. The lumen of the hollow needle continues through a central hole 63 in the grip.

Figure 4:
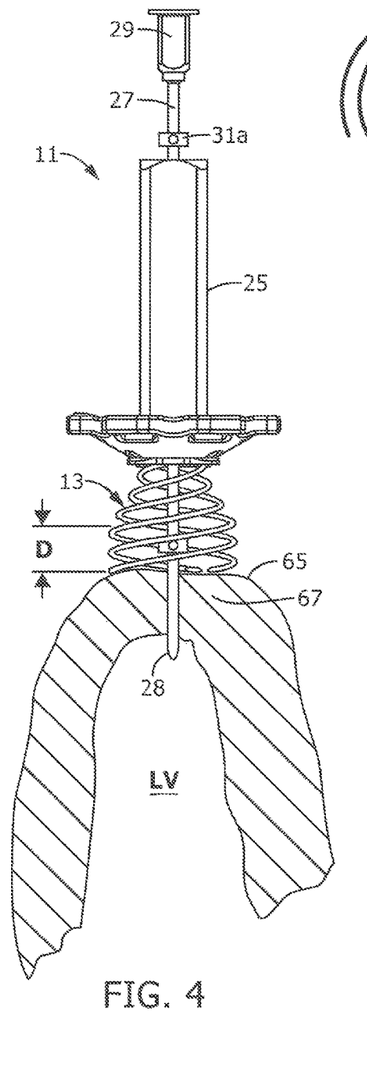
FIG. 4 is a schematic view of the device of FIG. 1 shown in association with the apex of a human heart with the pointed needle extending into the heart ventricle and with the distal end of the wire coil anchor just in contact with the outer surface of the heart tissue.

Additional features of the device 11 will become apparent by description of use of the device in one operational method, for example, a TAVI procedure where the left ventricle of the human heart is entered via the apex 65 of the heart. Such a sequence of operations is depicted in FIGS. 4-8A. The device 11 is inserted through an opening of the chest cavity of the patient and is positioned so that the distal end of the anchor 13 is juxtaposed with the surface of the heart wall 67 at its apex. The grip 29 is used to guide the pointed end 28 of the hollow needle into and through the wall 67 of the heart causing it to penetrate through the heart wall tissue so that its distal end is positioned within the left ventricle (LV), as depicted in FIG. 4. At this point, blood will begin to emerge from the proximal end of the hollow needle at the opening 63 in the grip.

With the device 11 so positioned, the surgeon rotates the handle to seat the anchor 13 in the heart wall tissue 67 in a stable orientation. The provision of the hollow needle 27 already in position provides a stable axis about which such rotative implantation can occur so that the wire coil 19 becomes precisely located, circumscribing the passage created in the heart wall 67 at the apex 65 by the penetration of the hollow needle.

Figure 5:
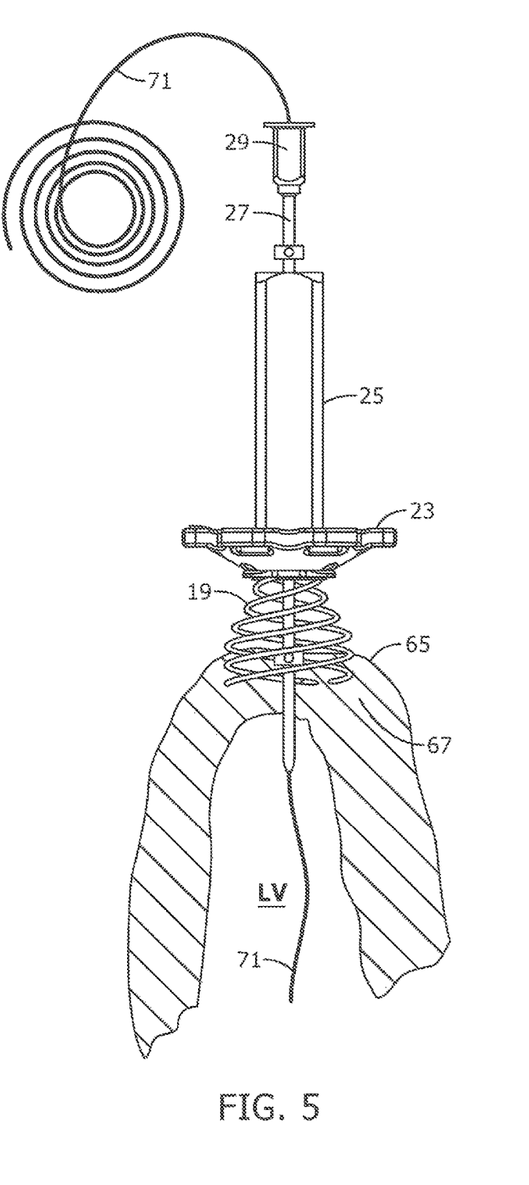
FIG. 5 is a view similar to FIG. 4 with the hollow needle extending into the ventricle, with the distal region of the wire coil anchor seated in the heart valve tissue, and with a guidewire extending into the ventricle.
Figures 14, 15, 20:
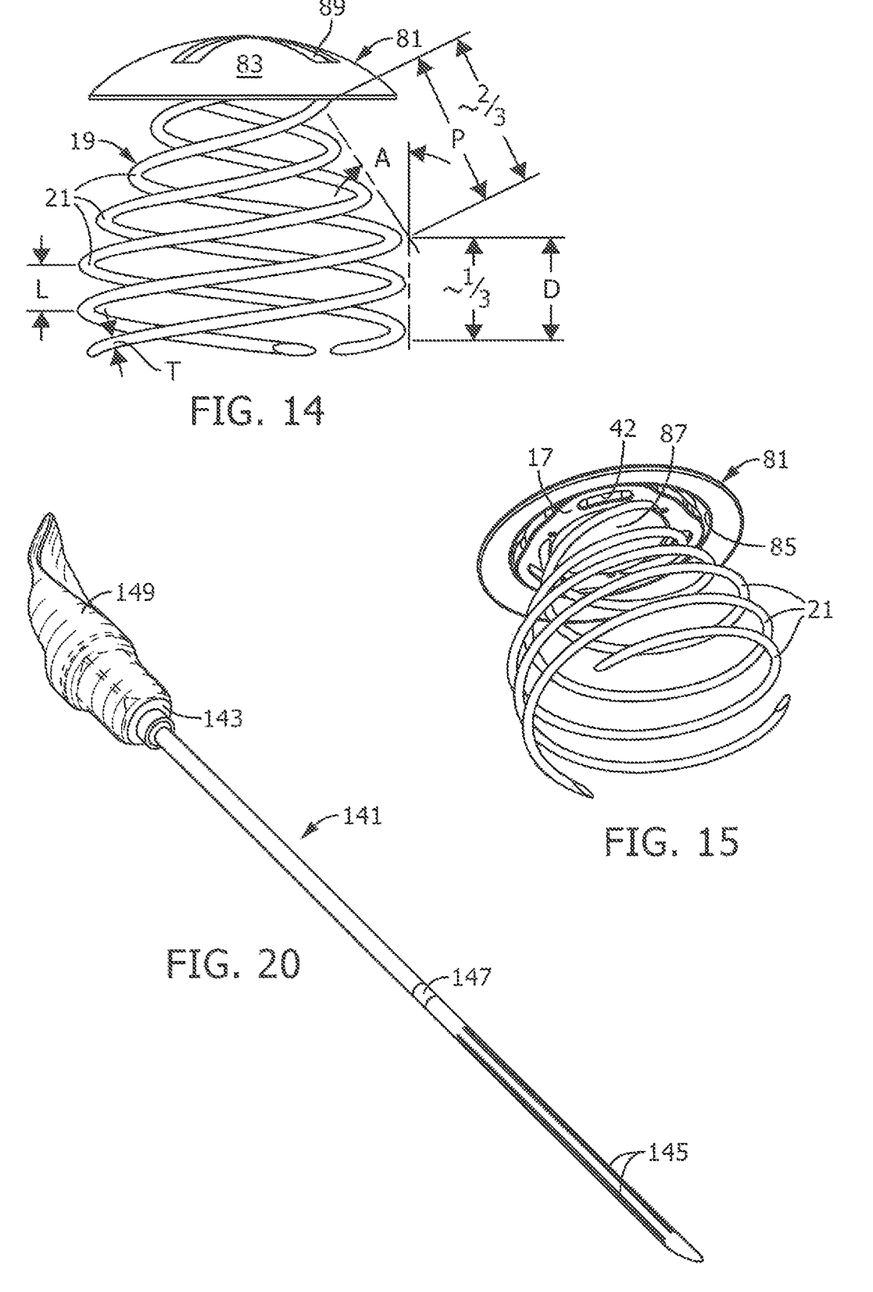
FIG. 14 is a front view of the anchor of the FIG. 1 device with a cap installed.
FIG. 15 is a perspective view of FIG. 14.
FIG. 20 is a perspective view of an alternative embodiment of a hollow needle that may be used in the device of FIG. 16.

The anchor 13 is preferably constructed in a manner best seen in FIG. 14. The anchor wire spiral is made of metal wire of circular diameter having a thickness T in the axial direction. Alternatively, it may be of an elliptical or like cross section. The anchor 13 is precisely constructed so that the axial spacing L between adjacent loops or turns of wire is at least three times T. This relationship has been found to provide an overall arrangement where the heart tissue, when subsequently pressed radially outward as a catheter is inserted, will not suffer damage to the tissue itself. Moreover, the wire spiral portion 19 of the anchor is formed with a distal tubular region D of substantially constant diameter and a frustoconical proximal region P that decreases from the constant diameter of the distal region and that will accordingly radially inwardly compress the heart wall tissue 67 to subsequently seal the access opening when caused to enter the heart tissue. The length of the distal constant diameter region D is preferably at least about ⅓ of the total axial length of the wire spiral, and it serves to first anchor the device in the organ wall. The angle A of the frustoconical sidewall of the proximal region of the wire spiral 19 is preferably about 30-40 degrees (see FIG. 14). The surgeon grips the extended guide section 25 and/or the handle base 23 and rotates the handle 15 sufficiently far to stably set the distal tubular region D of the wire spiral in the apical tissue as seen in FIG. 5, using the arrow 39 in the handle 35 as a reference point. When the anchor 13 is formed with three wire spiral sections 21 as illustrated in FIGS. 1-5, the device 11 may need to be rotated only about ¾ to 1 full turn to set the distal region D in the heart wall tissue.

With the device 11 so implanted, the stop 31b may seat against the apex, and a guidewire 71 is threaded through the hollow needle 27. The device 11 is shown in about this operative position in FIG. 5 where the distal end of the guidewire resides in the left ventricle (LV) of the heart, and it may also be further advanced through the aortic or other to-be-treated valve if desired. The guidewire 71 can be inserted into the LV anytime after the hollow needle point 28 has penetrated into the left ventricle, and it may be preferable to immediately insert the guidewire 71 at least through the hollow needle at such time. Because the guidewire can be selected so as to substantially fill the lumen of the hollow needle 27, it would defer the outflow of blood through the hollow needle while the device is being screwed into its stable position that is seen in FIG. 5.

Figure 6:
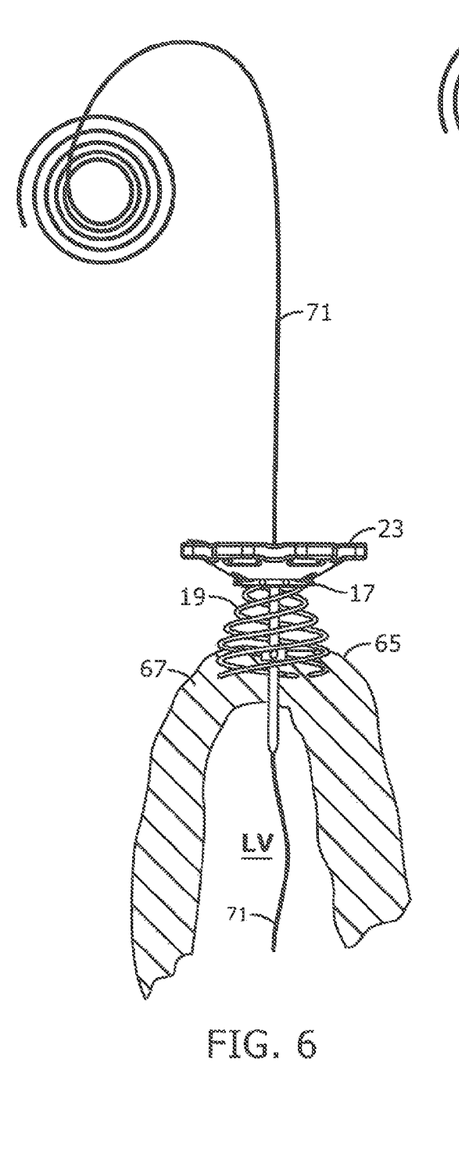
FIG. 6 is a view similar to FIG. 5 with the hollow needle and an extended guide removed and with the guidewire remaining in place extending into the ventricle.
Figure 6A:
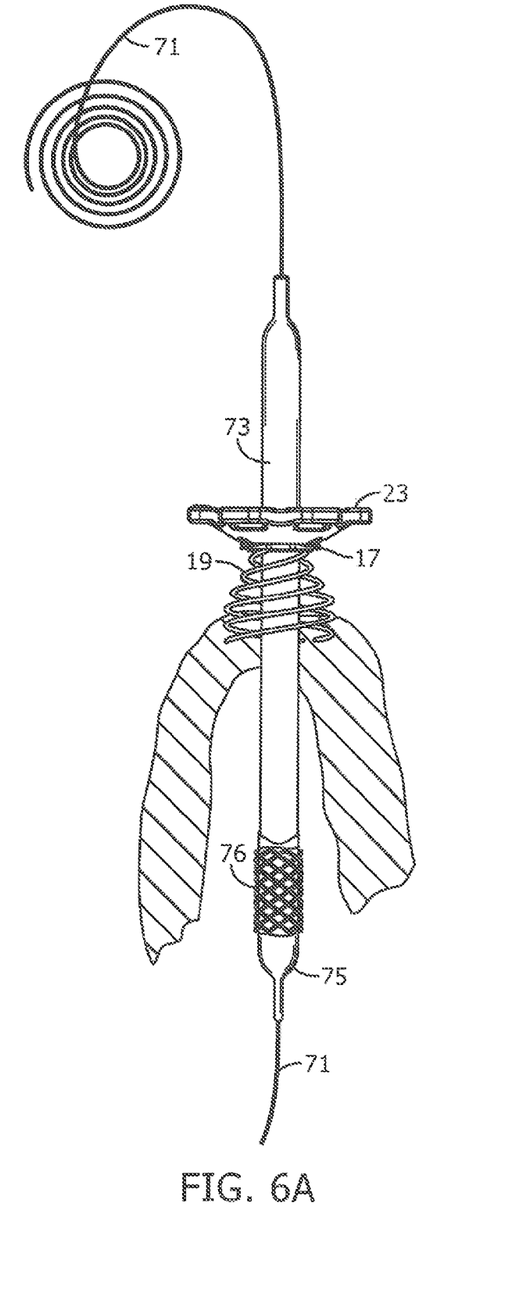
FIG. 6A is a view similar to FIG. 6 with the distal end of a catheter inserted through the apex of the heart over the guidewire.

With the flexible guidewire 71 in position, the hollow needle 27 is removed by first unscrewing the threaded distal end 55 of the extended guide section 25 from the interiorly threaded ring-shaped body 17 of the anchor. Upon removal of the hollow needle, the heart wall tissue presses at least slightly against the guidewire as seen in FIG. 6 and deters blood flow to some extent. Depending upon the operation to be carried out, a series of various types of catheters 73 with pointed distal ends 75 are inserted and exchanged over the guidewire 71, as seen in FIG. 6A, spreading the passage initially created by the hollow needle in the heart wall tissue at the apex radially outward within the general confines of the anchor 13 while preserving adequate hemostasis around the catheter. The central opening 47 through the handle base 23 and the threaded opening 57 of the ring-shaped body 17 are of sufficient diameter to permit the catheter 73 to slide therethrough. For example, the catheter may have an exterior diameter of about 12 mm in which case the interior threaded opening 57 of the ring-shaped body 17 of the anchor might be about 16 mm. The construction of the distal region of the wire spiral(s) enable outward tissue movement resulting from passage of the catheter and accommodates the large size catheter with little or no tissue damage. In this respect, the steep angle of the spiral wires and the spacing L between adjacent loops of the wire spiral are so designed as to permit the tissue to distend sufficiently radially outward (between the wire loops) to accommodate the passage of the catheter 73 with little or no permanent damage to the heart tissue at these locations.

The catheter 73 may carry a dilation balloon and a stent 76 that are to be deployed and opened inside a diseased natural aortic valve (see FIG. 6A). It may also contain a replacement valve along with the stent 76, or a first catheter may be withdrawn and a second catheter inserted over the guidewire 71 to deliver the replacement valve to interconnect within the stent. Alternatively, catheters may be used to deliver other devices to a cavity within the heart. Similarly, the device 11 could be used to provide an access opening to other bodily organs to allow a desired operation to be effected therewithin in a less invasive manner.

Figure 7:
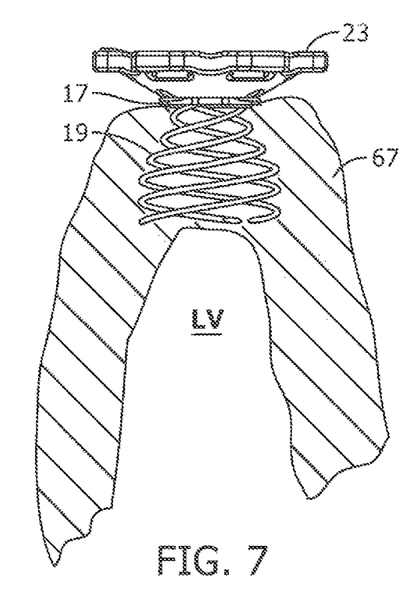
FIG. 7 is a view similar to FIG. 6 with the catheter and guidewire removed and with the anchor screwed completely into the apex of the heart to seal the passage created by the hollow needle and the catheter.

Once the operation within the left ventricle has been completed, e.g. by the implantation of the replacement aortic valve, the catheter 73 and the guidewire 71 are withdrawn, and the surgeon would then employ the handle base 23 to screw the anchor wire spiral 19 deeply into the heart valve tissue 67 at the apex. To deter potential initial bleeding, the surgeon may wish to begin to screw the proximal section P of the wire spiral into the apex while the pointed distal portion of the catheter is still within the confines of the wire spiral. The final result of this step is depicted in FIG. 7 where the entire proximal frustoconical section P of the coil is now embedded in the heart valve tissue, with the ring-shaped body 17 of the anchor seated in juxtaposition with the tissue surface. This maneuver can be promptly and readily carried out because the handle base 23 is already in place and attached to the anchor 13. The screwing of the wire spiral 19 deeply into the heart tissue 67 effectively closes and seals the passage which had been created through the wall of the heart. The heart wall tissue is uniformly radially inwardly compressed to seal this passage and achieve hemostasis. Tight sealing is achieved because of the precise location of the anchor wire spiral 19 relative to the central passage that was cut through the heart tissue; such precision is obtained when the spiral was initially located about the hollow needle as an axis assuring the desired precise centralization of the passage created by the needle within the wire spiral.

Figure 8:
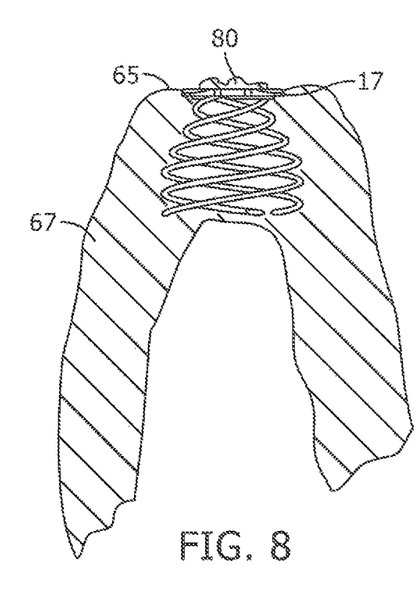
FIG. 8 is a view similar to FIG. 7 with the handle base removed from the anchor.
Figure 9:
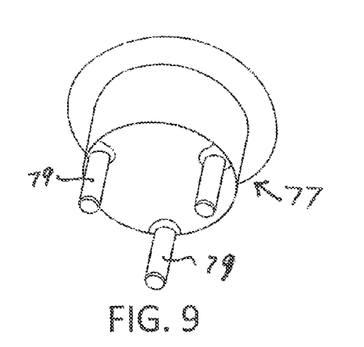
FIG. 9 is a perspective view of a disengaging or removal tool.
Figure 11:
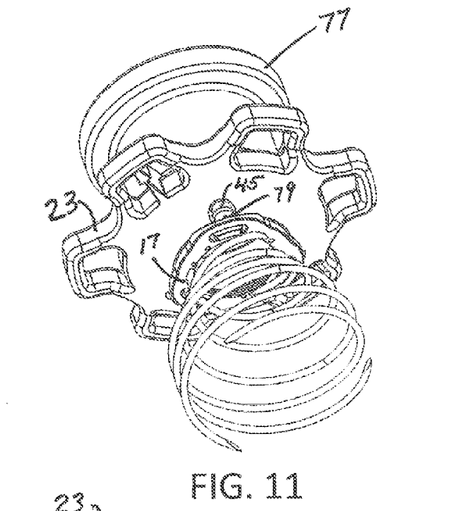
FIG. 11 is an assembly showing the disengaging tool of FIG. 9 mated with the detachable handle base of FIG. 10 with its three pegs extending through holes so as to contact the proximal surface of the ring-shaped body of the anchor.

To disengage the handle base 23 from the ring-shaped body 17 of the anchor, a disengaging tool or extractor 77 is provided, see FIG. 9. The extractor 77 is formed with three pegs 79 of circular cross section which are equiangularly located with their centers on a circle that is the same as that on which the centers of the three circular holes 45 in the handle base 23 are located. By mating the extractor 77 with the handle base 23, as depicted in FIG. 11, and pressing the two together, the three circular pegs 79 slide through the three holes 45 and engage the proximal surface of the ring-shaped body 17 at locations just radially outward of the three slots 42 in which the three prongs 41 were seated to the effect the press-fit interconnection between the handle base 23 and the ring-shaped body 17 of the anchor. As a result, the handle base 23 is easily separated from the ring of the anchor to arrive at the situation depicted in FIG. 8.

Figure 8A:
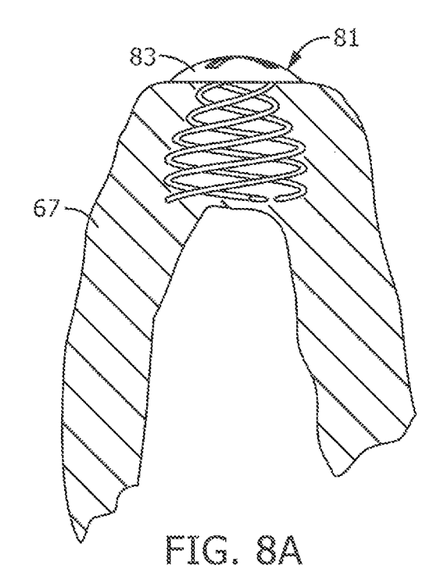
FIG. 8A is a view similar to FIG. 8, wherein a cap has been installed upon the anchor to provide a smoother, more physiological contour at the apex of the heart.

With the handle base 23 removed, FIG. 8 illustrates the anchor as it resides in place sealing the passage through the apex of the heart which was first created by the hollow needle and then expanded when the catheter 73 was inserted into the left ventricle over the guidewire 71. With the wire spiral 19 compressing the heart wall tissue as a result of the shape of the frustoconical upper region, a tip portion 80 of the apex tissue bulges through the central opening of the ring-shaped body 17 of the anchor. To further compress the heart wall tissue at this location, a cap 81 is provided (see FIGS. 14 and 15) which covers the ring-shaped body 17 of the anchor. The cap 81 has a spherical proximal or upper surface 83 and a distal or undersurface 85 which is formed with a cavity that accepts and receives the anchor ring-shaped body 17. The undersurface of the cap 81 includes a threaded central post 87 which has threads matching those of the threaded central opening 57 of the ring-shaped body 17. The proximal or upper surface has a pair of crossed grooves 89 that facilitate the screwing of the cap 81 in place to seat the threaded central post 87 in the central opening of the ring-shaped body and thus further compress the heart valve tissue at the very point of the passage's emergence from the apex 65 of the heart. This further compression positively seals this passage and guards against potential leakage of blood therefrom, assuring homeostasis. FIG. 8A shows the cap 81 in place with its upper surface 83 providing a smooth surface that guards against any potential abrasion of the pericardial sac within the chest cavity. One other option that might be given to the surgeon is to screw the spiral wire coil into the apex until satisfactory haemostasis achieved and then simply clip the rest of the protruding wire or wires at the epicardial surface, allowing thus slight retraction and complete disappearance of the wire tips from the epicardial surface.

FIGS. 14 and 15 show the cap 81 in place on the anchor 13 and also illustrate the preferred wire spiral 19, which utilizes three wire spiral sections 21. The use of three sections 21 with distal ends in the form of sharpened points located equiangularly at 120 degree intervals on the circle that constitutes the distal end of the anchor 13 has two advantages. It facilitates the precise entry of the sharpened distal tips into the heart tissue when rotated about the hollow needle as an axis, and it results in the placement of the wire coil uniformly spaced from the central passage that is created about the entire 360 degrees. The use of three wire sections 21 should improve stability of the anchoring and promote haemostasis, especially in older patients with fragile and thin myocardium. Such may also allow the entry angle of the sharp wire ends, relative to a plane perpendicular to the axis, to be increased; moreover, a lesser screwing rotation of the anchor 13 may be required to initially seat the distal ⅓ region D of the constant diameter in the heart valve tissue 67 to arrive at the arrangement depicted in FIGS. 5, 6 and 6A.

Although the use of 3 or more wire spiral sections 21 may be preferred for the reasons set forth above, basic advantages of the device 11 can be obtained by employing one or two wire spiral sections 21. Two alternative embodiments of anchors are illustrated in FIGS. 12 and 13, both of which employ a ring-shaped body 17 having a circular central opening 57, the interior wall of which is formed with threads 59. An anchor 13a is illustrated in FIG. 12 which employs 2 wire spiral sections 21a. An anchor 13b is illustrated in FIG. 13 which employs a single wire spiral section 21b. It can be seen that the anchors 13a and 13b will function in the same manner as the anchor 13 once press-fit to the handle base 23 through engagement with the interconnecting prongs 41 that are received in the three slots 42, and they will similarly engage with the threaded distal end 55 of the extended guide section of the handle 25.

If for any reason after the operation has been completed and the passage has been sealed by seating the cap 81 to positively close the passage, it becomes apparent at some time during the post-operative course that an entirely successful operation has not resulted so that it is necessary to re-enter the left ventricle, the device 11 allows such a re-entry to be readily performed through the previous chest wall incision. Using the crossed grooves 89 in the upper surface 83 of the cap, the cap is unscrewed and removed from the underlying ring-shaped body 17 of the anchor, and the handle base 23 is re-attached to the ring 17 by engaging the tabs 41 in the openings 42 in the ring. With the handle base 23 connected, the wire spiral 19 is unscrewed so that only the constant diameter distal section D remains in the heart tissue at the apex. This removes the pressure of the spiral loops compressing the tissue radially inward to seal the passage initially created by the hollow needle. The extended section 25 of the handle is then connected to the ring-shaped body 17, and it serves as a guide for re-insertion of the hollow needle 27. The alignment provided by the extended section 25 is such that the pointed tip 28 of the hollow needle 27 finds the central passage that was earlier created and follows it through the wall of the heart and into the left ventricle. A guidewire 71 is then inserted as before. Once a guidewire is again in place, the extended handle section 25 is removed, and a catheter 73 may then be inserted over the guidewire as before to reposition, improve or exchange the implant. Once the correction has been accomplished within the heart, the catheter 73 is withdrawn, and the closure procedure as described hereinbefore is repeated.

Figure 16:
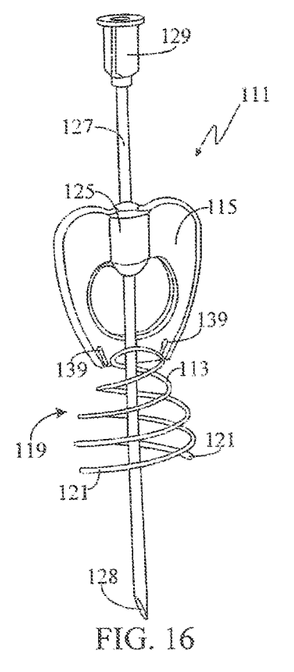
FIG. 16 is a perspective view of an alternative embodiment of a device embodying various features of the invention for providing temporary access into a human organ for the primary purpose of removing air that may have accumulated in such organ.
Figure 17:
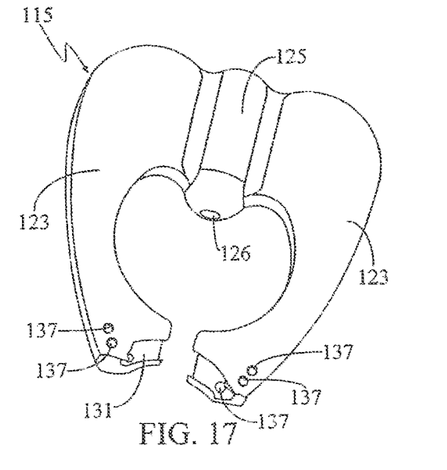
FIG. 17 is an enlarged perspective view of the detachable handle of the device of FIG. 16.

Illustrated in FIGS. 16-19 is an alternative embodiment of a device for providing temporary access to the ventricle of a heart and then closing such access or entry passage. The device 111 seen in FIG. 16 is designed for a simpler operation where a catheter will not likely be inserted into the ventricle of the heart to perform some function. Instead, the device 111 is expected to find its primary use in facilitating removal of air that might have accumulated in the left ventricle of the heart during any form of on-or-off pump coronary artery bypass surgery, closed or open heart procedures including valve repairs and replacements, and other aortic surgery, such as dissections, and other procedures carried out while the patient is on a heart-lung machine, and then readily and effectively closing the passage through which the air is removed. Such a device may be referred to as an implantable deairing device (IDD).

Figure 18:
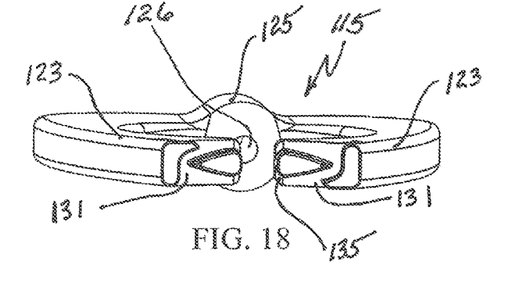
FIG. 18 is a perspective bottom view of the handle of FIG. 17.
Figure 19:
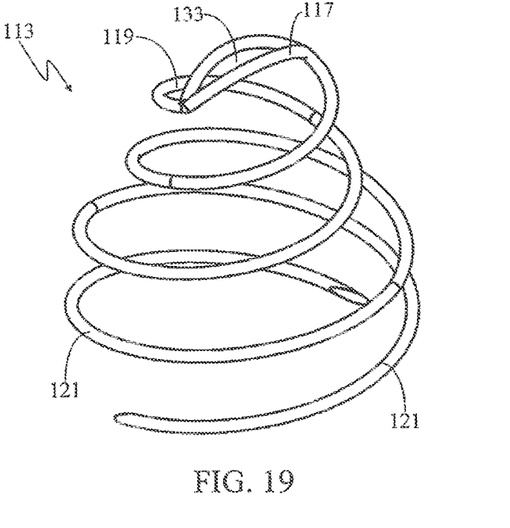
FIG. 19 is an enlarged perspective view of the anchor of the device of the FIG. 16.

The IDD 111 includes an anchor 113 and a handle 115. The anchor 113 includes a wire spiral 119 having a proximal interconnector section 117 from which two similar wire spiral sections 121 extend distally and terminate in pointed distal ends. The handle 115 is heart-shaped and includes a pair of curved arms 123 that extend distally from a central body. A central portion 125 of the heart-shaped body includes a central passageway 126 which accommodates a hollow needle 127 that is slidably inserted therethrough. The hollow needle 127 has a pointed distal end 128 and a grip 129 at its proximal end. The grip 129 may have a central opening which is an extension of the lumen of the hollow needle, or the hollow needle 127 may extend through the grip. The distal ends of the two arms 123 terminate in cavities 131 (FIG. 18) that are designed to accept the wire form interconnector 117 of the wire spiral so that the wire spiral 119 becomes linked to the handle 115. The two wire spiral sections 121, at the proximal arcuate ends, are mirror laser-welded to each other to form the interconnector 117 which has a central opening 133 to slidably receive the hollow needle 127. The interconnector opening 133 is aligned with the axis of the central passageway 126 and the spiral anchor 113, and the hollow needle 127 slides against the arcuate surfaces of the opening 133 and the facing flat wall surfaces 135 at the ends of the arms, which are seen in FIG. 18. The distal ends of the arms 123 of the handle are also provided with a plurality of holes or openings 137 through which suturing cords 139 are threaded and then tied to unite the detachable handle 115 to the anchor 113 as seen in FIG. 16.

The operation of the IDD 111 is generally similar to that described hereinbefore with respect to the device 11. With the chest cavity opened, the distal ends of the wire spiral sections 121 are placed in juxtaposition with the lifted apex of the heart, and the hollow needle 127 is caused to enter the heart tissue via its pointed end 128 through movement of the grip 129. The needle 127 is stabilized by its passage through the passageway 126 in the central body 125 of the handle, the walls 135 at the ends of the arms 123, and the walls of the opening 133 in the interconnector. With the pointed tip 128 of the needle residing in the left ventricle, the anchor 113 is screwed into the heart tissue by turning the handle 115 about the implanted needle 127 as an axis. This mounts the IDD stably in place while the deairing operation is effected. Once the surgeon is satisfied that substantially all of the air has been removed through the lumen of the hollow needle, the hollow needle 127 can be eased out slowly to thus assure the complete evacuation of the trapped air.

With the surgeon satisfied that all the air has been removed and the hollow needle 127 withdrawn, the handle 115 is turned clockwise to implant the anchor deeply into the heart tissue as described hereinbefore and effectively close the entry passage into the apex of the heart. The entry of the frustoconical proximal section of the wire spiral 119 compresses the heart tissue and seals the relatively narrow passage that was created by the hollow needle 127. The passage may be only three or four millimeters in outer diameter, and hemostasis is readily effected. With the anchor rotated so that the interconnector 117 is now in contact with the apex of the heart, the suturing cords 135 are cut in a manner so that they are retained on the arms 133 of the handle, and the detachable handle 115 is removed. This leaves only the smooth arcuate surfaces of the interconnector 117 extending from the apex of the heart; such should be acceptable and not cause complications within the chest cavity. Thus, it can be seen that the IDD provides a simple arrangement for removing air which has accumulated within the left ventricle of the heart as a result of other operations being carried out on the patient.

Generally, at the end of any heart operation and prior to reactivation of the heart, the evacuation of air that will have accumulated inside the left ventricle throughout the procedure is removed as follows. Without having a hollow needle device, such as the device 111, extending into the left ventricle, the surgeon lifts the apex of the heart as vertically as possible with his left palm to allow the accumulated air and air bubbles to rise to the highest point inside the left ventricle adjacent to the apex. Then while doing so, he either stabs or punctures the highest point in the apex with a large diameter hollow needle. Blood then starts appearing at the proximal end of the needle, and to further encourage the flow of blood from the needle, he helps by gently squeezing the left ventricle. However, blood being extracted through the needle comes from an unknown level of blood inside the left ventricle which probably is, in most cases, below the accumulated air level inside the left ventricle. Moreover, while squeezing and emptying left ventricle blood through a hollow needle is a relatively fast procedure, the complete refilling of the heart is a far slower procedure. Consequently, upon the ultimate release of applied external pressure by the surgeon upon the left ventricle, the compliance of the left ventricle instantaneously creates a negative pressure inside the left ventricle. As a result, in most cases, some room-air is sucked back into the left ventricle through the very same needle while the left ventricle is slowly refilling completely with blood.

It can be understood that using the device 111, or any hollow needle, the air that is being evacuated must enter the needle at the open tip 128. Therefore, it becomes important that the surgeon be able to align the needle so that the tip resides at the highest point of the left ventricle where the major air bubble has accumulated. Whereas a skilled surgeon may be able to adequately effect this task, the employment of an alternative embodiment of a needle 141 can substantially reduce the difficulty of achieving complete evacuation of air from the left ventricle.

Shown in FIG. 20 is an alternative hollow needle 141 which has a grip section 143 at its proximal end similar to that described hereinbefore, but in addition to being open at its pointed tip, it is also provided with a plurality of longitudinally or obliquely extending slots 145, which may be continuous or interrupted and extend along its length near the distal end of the needle. As a result, air and blood containing small air bubbles can enter the needle at any level, especially just under the apical inner wall and over a far greater depth and distance, thus providing a flow path for air in the evacuation of accumulated air from the left ventricle much greater and more effective than a comparable needle open only at the pointed end. To additionally assist the surgeon to appropriately orient the needle within the left ventricle, a penetration depth marker 147, in the form of a band or other indicia around the outer surface of the needle, is provided which may be spaced, for example, about 6 to 7 mm proximally of the beginning of the elongated slots 145. This distance would be slightly less than the minimal wall thickness at the apex of the average human heart. Accordingly, during an air evacuation procedure employing the needle 141, the surgeon would introduce the needle beyond the depth marker and then begin to extract the needle until the depth marker appears. At this point, he would halt removal knowing that all of the slots should now be capable of evacuating air and blood from the left ventricle. When he is confident that complete deairing has been accomplished, the needle 141 would be quickly removed, and while positive pressure is maintained on the left ventricle so some blood flow remains to avoid potential return of air, the handle would be used to screw the wire spiral into position to complete apical haemostasis as described hereinbefore.

As a further improvement, a unidirectional duckbill check-valve 149 may be added at the proximal end of the hollow needle 141. Shown in FIG. 20 is such a duckbill valve 149 that is formed from a thin latex or other polymer tubing, which is sufficiently elastomeric to fit about the grip 143 and of a strength such as to readily allow blood flow from the hollow needle to exit. However, if at any time a negative pressure would occur within the left ventricle, the duckbill valve 149 would close and prohibit any entry of room-air back into the proximal end of the hollow needle and through it into the left ventricle.

Although the invention has been described with respect to several preferred embodiments which constitute the best mode known at this time to the inventor to carrying out this invention, it should be understood that various changes and modifications as would be obvious to those skilled in this art could be made without deviating from the scope of the invention which is set forth in the claims appended hereto. For example, instead of securing the hollow needle 27 to the detachable handle 15 and limiting its relative movement with respect to the handle and the anchor by the use of a pair of collars 31a and 31b, the extended guide section 25 of the handle could be made in two pieces with an extended longitudinal central region wherein a flange attached to the hollow needle might slide along with the needle and in this way limit the axial distance the hollow needle can be moved relative to the handle. Similarly, inasmuch as the handle base 23 is attached securely to the ring 17 of the anchor by the press-fit arrangement, instead of connecting the detachable extended guide section 25 of the handle directly to the ring-shaped body 17 of the anchor, the guide section might instead be detachably interconnected to the handle base 23. Instead of using wire of circular cross section for the spiral sections 21, wire of oval or arcuate cross section may be used that would have a dimension at least about 50% greater in the axial direction of the spiral as compared to the radial direction. Other such changes will also be apparent upon study of the illustrated embodiments.

Particular features of the invention are emphasized in the claims which follow.

The invention claimed is:

1. A device for providing temporary access to the heart through a tissue wall of the heart, the device comprising:
    an anchor having a ring-shaped body having a central opening and at least one wire spiral having a pointed distal end and having a proximal end that is connected to said body, the at least one wire spiral being shaped for juxtaposition with the exterior surface of the wall of the heart and the at least one wire spiral having a distal tubular region of substantially constant diameter and a frustoconical proximal region that decreases from the distal tubular region,
    a detachable handle having a base formed with a central aperture and an interconnection means linking said base to said anchor,
    said handle including an elongated guide section that is formed with an elongated central passageway open at opposite ends,
    an elongated, hollow needle having a pointed tip for insertion through the wall of the heart so as to enter the heart, the needle being slidably received in said elongated central passageway, and
    means securing said hollow needle to said guide section for limiting the distance said hollow needle can be axially moved within said guide section while locating said pointed tip so that it penetrates the heart wall before said wire spiral makes contact with the exterior surface of the wall of the heart,
    whereby, once said needle is caused to penetrate into the heart, the device can be readily attached to the heart wall by screwing the wire spiral into the tissue wall of the heart via rotation relative to an axis coinciding with said needle, so that the device will then provide access to the heart along a guide wire that extends through said anchor, the guide wire being insertable through the lumen of the hollow needle before the hollow needle is withdrawn.

2. The access device according to claim 1 wherein said anchor includes a plurality of wire spirals connected to said ring-shaped body with their pointed distal ends spaced generally equiangularly with respect to one another.

3. The access device of claim 2 wherein each of said wire spirals has an arc length between about 400° and 700°.

4. The access device of claim 2 wherein two, three or four wire spirals are connected to said body, the wire spirals having proximal sections that grow greater in diameter in the distal direction.

5. The access device of claim 1 wherein said wire spiral is formed of wire having an axial thickness less than one-third of axial open distance between adjacent turns of the spiral in the distal tubular section.

6. The access device of claim 1 wherein said wire spiral is formed of wire of noncircular cross section that is contoured so as to have an inward-facing surface of a breadth at least about twice its radial thickness so as to promote inward compression of the heart wall tissue when the device is rotated to cause said anchor body to abut against the exterior surface of the wall of the heart.

7. The access device of claim 1 wherein said anchor body comprises a generally flat ring having angularly spaced apertures.

8. The access device of claim 7 wherein said interconnection means of said detachable handle is formed to press-fit with said anchor body at said apertures and wherein said handle main body has openings at equiangularly spaced locations.

9. The access device according to claim 8 in combination with a removal tool formed with parts for protrusion through said openings in said handle base to effect detachment of said handle base from said anchor.

10. The access device of claim 7 in combination with a cap for mating with said anchor body to close its central opening and seat against the wall of the heart upon conclusion of a surgical operation requiring such temporary access.

11. The access device according to claim 1 wherein said elongated guide section has a distal end that is formed for rotative engagement and disengagement with either the opening of said ring-shaped body or said central aperture of said handle base.

12. The access device according to claim 11 wherein said ring-shaped body has a threaded central opening, wherein said distal end of said elongated guide section has mating threads that interengage therewith, and wherein a separate cap for closing the central opening also has mating threads and is shaped surround the proximal surface of said ring-shaped body.

13. The access device of claim 1 wherein said at least one wire spiral has a conical proximal section and a tubular distal section, the tubular section extending for at least about 1/3 of the axial length of said wire spiral.

14. A device for providing temporary access to a ventricle of the heart through a wall at an apex of the heart, the device comprising:
an anchor having a ring-shaped body having a central opening and at least one wire spiral having a pointed distal end and having a proximal end that is connected to said body, the at least one wire spiral being shaped for juxtaposition with an exterior surface of the apex of the heart and the at least one wire spiral having a conical proximal section and a tubular distal section of substantially constant diameter,
a detachable handle having a base formed with a central aperture and an interconnection means linking said base to said anchor,
said handle including an elongated guide section that is formed with an elongated central passageway open at opposite ends,
an elongated, hollow needle having a pointed tip for insertion through the wall of the heart so as to enter a ventricle thereof, the needle being slidably received in said elongated central passageway, and means securing said hollow needle to said guide section for limiting the distance said hollow needle can be axially moved within said guide section while locating said pointed hp so that it penetrates the heart tissue before said wire spiral makes contact with the heart outer surface,
whereby, once said needle is caused to penetrate into the heart ventricle, the device can be readily attached to the heart wall at the apex by screwing the wire spiral into the tissue wall of the heart via rotation relative to an axis coinciding with said needle, so that the device will then provide access to the heart ventricle along a guide wire that extends through said anchor, the guide wire being insertable through the lumen of the hollow needle before the hollow needle is withdrawn;
wherein said anchor includes a plurality of wire spirals connected to said ring-shaped body with their pointed distal ends spaced generally equiangularly with respect to one another, and wherein two, three or four wire spirals are connected to said body, the wire spirals having proximal sections that grow greater in diameter in the distal direction;
wherein said wire spirals each have a conical proximal section and a tubular distal section, the tubular section extending for at least about A of the axial length of sad wire spiral.

15. A device for providing a temporary access opening into a human heart and then closing such access opening, the device comprising:
an anchor comprising a wire spiral formed of at least two spiral sections each having a pointed distal end, with proximal ends of said spiral sections inter-connected relative to one another, the wire spiral being shaped for juxtaposition with the exterior surface of the heart,
a detachable handle having a central passageway that is aligned axially of the wire spiral, said handle and said anchor being formed for detachable interconnection with each other, and
an elongated, hollow needle having a pointed tip for insertion through a wall of the heart so as to enter a cavity therewithin, said handle central passageway positioned to guide movement of said hollow needle axially within said wire spiral,
whereby said needle is slidable within said handle and once having entered the heart provides an axis about which said wire spiral can be screwed into the wall of the heart about said needle,
wherein said wire spiral is so shaped that it has a distal tubular region of substantially constant diameter and a frustoconical proximal region that decreases from the distal tubular region such that the anchor has a first position, spaced a first distance relative to the wall of the heart, whereby the distal tubular region is positioned to allow for dilation of the tissue wall to form an access opening in the tissue wall, and the anchor also has a second position, closer to the wall of the heart as compared to the first distance, whereby the anchor can selectively close the access opening by further rotating the wire spiral so that the tissue is progressively compressed radially inward using the frustoconical proximal region of the wire spiral.

\* \* \* \* \*